United States Patent [19]

Rosen et al.

[11] 4,364,126
[45] Dec. 21, 1982

[54] HEART VALVE WITH REMOVABLE CUSP PROTECTOR BAND

[75] Inventors: Jonathan J. Rosen, Fountain Valley; George M. Acosta, Long Beach; Christopher J. Bowman, Newport Beach, all of Calif.

[73] Assignee: Vascor, Inc., Anaheim, Calif.

[21] Appl. No.: 287,606

[22] Filed: Jul. 28, 1981

[51] Int. Cl.³ .............................................. A61F 1/22
[52] U.S. Cl. ...................................................... 3/1.5
[58] Field of Search ..................... 3/1.5, 1; 128/334 R

[56] References Cited

U.S. PATENT DOCUMENTS

| | | | |
|---|---|---|---|
| 3,130,419 | 4/1964 | Edwards | 3/1.5 |
| 3,551,913 | 1/1971 | Shiley et al. | 3/1.5 |
| 4,084,268 | 4/1978 | Ionescu et al. | 3/1.5 |
| 4,106,129 | 8/1978 | Carpentier et al. | 3/1.5 |
| 4,172,295 | 10/1979 | Batten | 3/1.5 |
| 4,222,126 | 9/1980 | Boretos et al. | 3/1.5 |

FOREIGN PATENT DOCUMENTS 1016811  1/1966  United Kingdom ..................... 3/1.5

Primary Examiner—Ronald L. Frinks
Attorney, Agent, or Firm—Wayne R. Eberhardt

[57] ABSTRACT

A plastic band is secured around the outside of a prosthetic heart valve adjacent the sewing cushion to protect the valve leaflet material against inadvertent needle punctures and tears while sutures are being placed through the sewing cushion. The band is held in place by a single retention suture which passes through the band and sewing cushion of the valve and extends across the valve orifice. The protector is especially desirable for use with pericardial tissue valves having the tissue mounted on the outside of the valve stent where the tissue is particularly exposed and susceptible to needle damage.

18 Claims, 6 Drawing Figures

U.S. Patent
Dec. 21, 1982
4,364,126
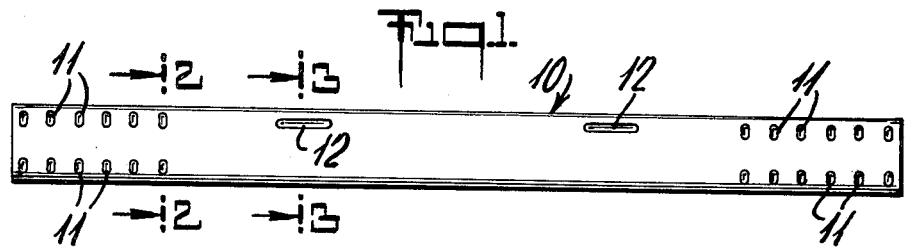
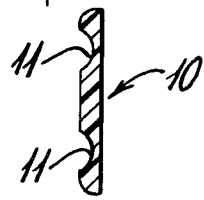 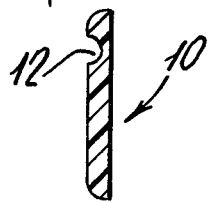
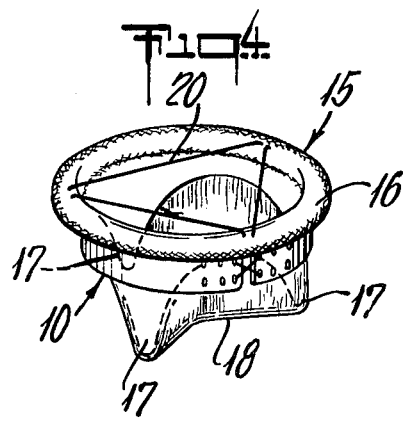
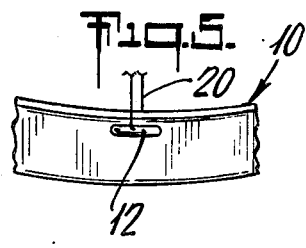 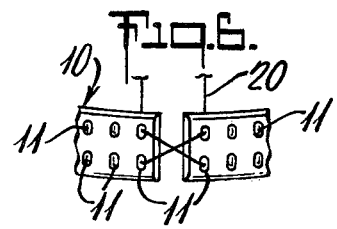

HEART VALVE WITH REMOVABLE CUSP PROTECTOR BAND

BACKGROUND OF INVENTION

1. Field of the Invention

This invention relates to prosthetic heart valves and, more particularly, to an apparatus and method for protecting valve cusp material against inadvertent needle puncture or tear during the implantation of the valve in the patient.

2. Description of Prior Art

Prosthetic tissue heart valves constructed of autologous or hemologous fascia lata, dura matter or heterologous pericardium are described in U.S. Pat. Nos. 4,084,268 and 4,172,295. Typically, such valves are constructed by securing the tissue around the outside of a valve stent or framework having a circular base at one end and three axially-extending commissure posts interconnected by valleys at the other end. The tissue is supported at three points by the stent posts while the tissue intermediate the stent posts extends through the valleys and into the center of the stent to form three valve cusps.

The valve stent also includes a sewing cushion around the circular base portion as illustrated in the above-referenced patents. The sewing cushion provides a means for attaching the valve to the patient by suturing through the sewing cushion. In one method of implanting the valve, a plurality of sutures are placed through the sewing cushion and the mounting site in the patient using an interrupted mattress stitch while holding the valve several inches away from the mounting site. When all the sutures are in place, the valve is guided down the suture lines into the mounting position and the sutures are tied off.

In the case of valves constructed of pericardium or other natural tissues, the tissue is positioned outside the stent as illustrated in the above-referenced patents. The tissue is thusly exposed and subject to needle damage as the mounting sutures are placed through the sewing ring. Since the operating area is cramped and vision may be limited, especially in the case of mitral valve replacement where the cusps of the valve are directed away from the surgeon and shielded from view by the sewing ring, great care must be taken when passing the mounting sutures through the sewing ring to avoid accidentally piercing or tearing the valve tissue. Because of the delicate nature of the tissue, a single needle hole can seriously compromise the long-term performance and durability of the valve.

It is accordingly an object of the present invention to provide a method and device for protecting the cusp material of a prosthetic heart valve against needle damage during the installation procedure. It is a further object of the present invention to provide a protective device which is easily removed from the heart valve after all the mounting sutures are in place. These and other objects of the present invention will be apparent from the ensuing description and claims.

SUMMARY OF THE INVENTION

Pericardial and other prosthetic tissue heart valves susceptible to needle damage during installation are protected from such damage by providing a protective band to surround and cover the valve tissue immediately adjacent the sewing cushion. The protector may consist of a strip of plastic material which is formed into a cylinder and secured to the valve by a single retention suture. The suture is attached to the protective band at each end and at one or more points between the ends, traversing the valve by passing through the sewing ring and across the valve orifice.

The retention suture traversing the orifice of the valve is highly visible and assures that the valve will not be inadvertently be installed with the protector in place. Once all the mounting sutures have been positioned through the sewing ring, the protector is removed by cutting the retention suture in the area of the valve orifice and pulling it free of the valve and protective band. Once the retention suture has been removed, the protector is readily withdrawn from between the mounting sutures.

To facilitate suturing through the protector, the plastic strip is provided with a plurality of dimples and/or channels having a thin base-thickness at its ends and midpoint. Multiple rows of dimples or channels across the width of the strip are provided at either end to permit the length of the strip to be adjusted to the circumference of the valve by cutting off excess strip material.

DESCRIPTION OF DRAWINGS

FIG. 1 is a plan view of a protective band.

FIG. 2 is a cross-sectional view of the protective band through line 2—2 of FIG. 1.

FIG. 3 is a cross-sectional view of the protective band through line 3—3 of FIG. 1.

FIG. 4 is a view in perspective of a mitral valve with the protective band in position.

FIG. 5 is a partial view showing the suture placement at a point between the ends of the protective band.

FIG. 6 is a partial view showing the suture placement at the ends of the protective band.

DESCRIPTION

Referring now to FIG. 1 there is illustrated at 10 a side plan view of a protective band of the present invention comprising a strip of plastic sheet material, suitably polypropylene, having a length corresponding to the outside circumference of the prosthetic tissue heart valve. The width of the strip is preferably at least about 0.25 inches, and the thickness is about 0.02 inches. On one side at each end of the band are located suture guide means in the form of a double row of circular depressions 11 centrally disposed about the major axis of said strip and extending inward from the ends in a spaced relationship over a distance of at least about 0.5 inches. Between the ends of the band and aligned with one row of circular depressions are elongated depressions 12 which are preferably about 0.25 inches long. Each depression has a base thickness of less than about 0.01 inches as illustrated in FIGS. 2 and 3 which are cross-sectional views at lines 2—2 and 3—3 respectively of FIG. 1.

The protective band is affixed to the heart valve as illustrated in FIG. 4 which is a view in perspective of a mitral heart valve with the protective band in place. Referring to FIG. 4, retention suture 20 passes through both ends of the protective band and through the sewing ring 16 of the valve and across the valve orifice. The intermediate portion of the band, hidden from view in FIG. 4, is secured at two points by the suture as illustrated in FIG. 5, the suture passing through the thin-base portion of elongated depressions 12 and thence returning through the sewing cushion. At the ends of the protective band, the suture passes through the outermost circular depressions in a figure X as illustrated in FIG. 6. The suture is always placed through the outermost row of depressions at the end of the protective band, and multiple depressions are provided to enable the band to be shortened if necessary to fit smaller size valves by cutting off appropriate end sections at one or both ends of the protective strip.

The circular and elongated depressions in the band facilitate the suture attachment of the band to the valve since the thin areas in the base of the depressions are easily pierced by a surgical needle.

The preferred material for band construction is polypropylene which is soft and flexible, easily molded and easily stitched. Other suitable materials include polyethylene, nylon, polyvinylchloride and other nontoxic polymeric compositions which possess the desirable combination of physical properties.

The protective band is intended primarily for use on heart valves constructed of natural or synthetic sheet materials such as pericardium, fascia lata, dura matter or polyurethane, and where the construction of the valve places the sheet material on the outside of the valve stent where it is particularly exposed and susceptible to needle damage. The band may, of course, also be used in conjunction with porcine heart valves where, although the valve tissue is contained within the confines of the stent, the needles of the mounting sutures may catch in the fabric of the stent cover and interfere with suture placement.

When attaching the protective band to the valve, the ends of the band are butted together and secured with a double armed suture. The band is then positioned on the valve and both ends of the suture passed through the sewing ring and over the valve annulus. One end of the suture proceeds through the sewing ring and intermediate depressions 12 as illustrated in FIG. 4. The two ends of the suture are finally tied so the knot is located over the valve orifice.

The protective band is removed by cutting one strand of the retention suture at a point over the valve orifice. When an interrupted mattress stitch is used for a valve installation, the band is not removed until all the sutures have been placed through the sewing ring. When a continuous or semicontinuous suturing technique is used to sew the valve directly in place, the band is removed before the valve is positioned for suturing.

While the foregoing description has been directed to a preferred embodiment of the protective band of the present invention, it will be appreciated that certain variations thereof which are functionally equivalent are also included within the scope of the invention. For example, the circular depressions illustrated in the Figures as suture guide means may be converted to openings extending through the band, and the suture threaded through these openings rather than being sewn through the band material. In another alternative embodiment, the double row of circular depressions at the ends of the strip may be replaced by a plurality of single, elongated depressions extending across the width of the band, or by a pair of elongated channels extending lengthwise along either side of the central axis of the band. A singular elongated depression 12 located at the midpoint of the protective strip may also be used rather than the pair of depressions as illustrated in FIG. 1. These and other variations will be apparent to those skilled in the art in view of the disclosure contained herein.

We claim:

1. In a prosthetic heart valve comprising a cylindrical stent, sheet material overlying the stent and extending inwardly to form a closure within the confines of said stent, and a sewing cushion encircling the stent at one end thereof, the improvement comprising a removable protective band circumscribing the stent and overlying the sheet material immediately adjacent said sewing cushion.

2. The valve of claim 1 wherein said protective band is secured to said valve by means of a single retention suture passing through the band and sewing cushion and traversing the orifice of the valve.

3. The valve of claim 1 wherein the band is fabricated of a polymeric material.

4. The valve of claim 3 wherein said protective band is molded of polypropylene.

5. The valve of claim 2 wherein said protective band includes depressions at locations where the suture is passed through the band.

6. The valve of claim 2 wherein said band includes openings at locations where the suture is passed through the band.

7. The valve of claim 2 wherein the protective band comprises an elongated strip formed into a cylinder with the ends secured by said retention suture.

8. The valve of claim 1 wherein said protective band is at least about 0.25 inches wide.

9. The valve of claim 1 wherein said sheet material is a natural tissue material.

10. The valve of claim 8 wherein said natural tissue material is selected from the group consisting of pericardium, fascia lata and dura matter.

11. The valve of claim 1 wherein said sheet material is polyurethane.

12. A protective band adapted to circumscribe a prosthetic heart valve constructed of natural or synthetic sheet material and comprising a flat, elongated strip having a length corresponding to the circumference of said valve a width of at least about 0.25 inches, said band having a plurality of suture guide means at each end thereof and at least one suture guide means intermediate said ends.

13. A protective band of claim 12 wherein said strip is fabricated of a nontoxic polymeric material.

14. The protective band of claim 13 wherein said protective band is molded of polypropylene.

15. The protective band of claim 12 wherein said suture guide means comprise openings through said strip.

16. The protective band of claim 12 wherein said suture guide means comprise depressions in one surface of said strip.

17. The protective band of claim 16 wherein the thickness of said strip is about 0.02 inches, and the thickness at the base of said depressions is less than about 0.01 inches.

18. The protective strip of claim 12 wherein said strip includes a double row of suture guide means centrally disposed about the major axis of said strip at each end thereof and a pair of elongated suture guide means aligned with one of said rows and equidistantly spaced between the ends of said strip.

* * * * *